United States Patent [19]

Alt et al.

[11] Patent Number: 4,618,357
[45] Date of Patent: Oct. 21, 1986

[54] NOVEL ALKENYL ACETAMIDES AND THEIR USE IN THE REGULATION OF THE NATURAL GROWTH OR DEVELOPMENT OF TURF GRASS

[75] Inventors: Gerhard H. Alt, University City; John P. Chupp, Kirkwood; Lane A. Clizbe, Chesterfield, all of Mo.

[73] Assignee: Monsanto Company, St. Louis, Mo.

[21] Appl. No.: 701,272

[22] Filed: Feb. 13, 1985

[51] Int. Cl.[4] .......................................... A01N 37/118
[52] U.S. Cl. ......................................... 71/76; 71/88; 71/98; 71/106; 71/118; 71/119; 71/120; 71/100; 260/513.5; 549/487; 560/30; 564/48; 564/57; 564/59; 564/154; 564/155
[58] Field of Search ................................... 71/76, 118

[56] References Cited

U.S. PATENT DOCUMENTS

| | | | |
|---|---|---|---|
| 3,586,496 | 6/1971 | Chupp | 71/118 |
| 3,829,306 | 8/1974 | Ratts | 71/76 |
| 3,830,841 | 8/1974 | Ratts | 71/118 |
| 4,392,884 | 7/1983 | Pallos et al. | 71/118 |

Primary Examiner—Catherine L. Mills
Attorney, Agent, or Firm—Frank D. Shearin; Robert B. Martin

[57] ABSTRACT

The growth of turf grass can be retarded by applying to said turf grass an effective growth retarding amount of a compound of the formula:

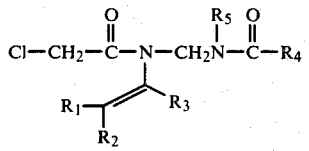

wherein $R_1$, $R_2$, and $R_3$ are independently hydrogen, halogen, $C_{1-6}$ alkyl, or haloalkyl; $R_4$ is hydrogen; $C_{1-4}$ alkyl, alkenyl, alkoxy, haloalkyl; $C_{1-2}$ alkylamino, $C_{1-2}$ alkylthio, $C_{2-4}$ cycloalkyl, $C_{2-6}$ alkoxyalkyl, $C_{2-6}$ alkylthiomethyl, amino, phenoxy, phenamino, or furan; and $R_5$ is hydrogen or $C_{1-4}$ alkyl.

8 Claims, No Drawings

NOVEL ALKENYL ACETAMIDES AND THEIR USE IN THE REGULATION OF THE NATURAL GROWTH OR DEVELOPMENT OF TURF GRASS

FIELD OF THE INVENTION

The invention herein pertains to novel alkenyl acetamides and the use of these acetamides to regulate the natural growth or development of turf grass.

BACKGROUND OF THE INVENTION

Many compounds are known in the art that regulate the natural growth of turf grass. Unfortunately, most of these compounds have associated activity which prevents their widespread use. Some of the compounds are phytotoxic causing discoloration and thinning of the turf grass with the regulation of the natural growth. Other compounds suffer from unexplainable inconsistent biological activity. Still other compounds have a low margin of safety which results in phytotoxicity in overlapped areas or with incorrect usage. However, the need for such growth regulating chemicals is increasing in areas difficult to mow, such as roadsides, hills and the like. Chemicals with less phytotoxicity, more uniform biological activity, and greater margin of safety are desirable to enable effective management of turf grass.

SUMMARY OF THE INVENTION

The present invention relates to a novel class of acyclic alken-1-yl acetamides and the method of using these compounds for regulating the natural growth of turf grass. The novel compounds of the present invention are represented by the formula:

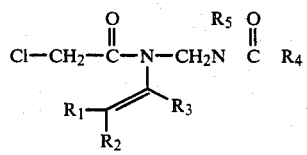

wherein $R_1$, $R_2$, and $R_3$ are independently hydrogen, halogen, $C_{1-6}$ alkyl, or haloalkyl; $R_4$ is hydrogen; $C_{1-4}$ alkyl, alkenyl, alkoxy, haloalkyl; $C_{1-2}$ alkylamino, $C_{1-2}$ alkylthio, $C_{3-4}$ cycloalkyl, $C_{2-6}$ alkoxyalkyl, $C_{2-6}$ alkylthiomethyl, amino, phenoxy, phenamino, or furan and $R_5$ is hydrogen or $C_{1-4}$ alkyl.

The method of the present invention involves regulating the natural growth of turf grass by applying to the grass an effective plant-regulating, nonlethal amount of a compound of the present invention.

The term "turf grass" is generally considered as encompassing a variety of both warm and cool season grasses which are employed in the development and/or management of certain areas for specific purposes, such as utility, beautification, and recreation. Examples of such turf grass include Tall Fescue, Red Fescue, Kentucky Blue Grass, Bermuda Grass, St. Augustine Grass and the like. Among the areas in which turf grasses are most frequently used are roadsides, golf courses, parks, and grounds which surround large educational or industrial institutions and, of course, the lawn of homeowners. In all of such areas it is readily apparent that a chemical treatment which serves to regulate the growth of turf grass is highly desirable since it will serve to minimize the time and cost expended on maintenance. A more thorough disclosure of the present invention is presented in the detailed description which follows.

DETAILED DESCRIPTION OF THE INVENTION

The present invention relates to novel acyclic alken-1-yl acetamides and a method for regulating the growth of turf grass by application of these compounds to the turf grass. The compounds of the present invention have the formula:

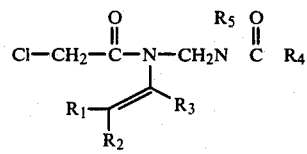

wherein $R_1$, $R_2$, and $R_3$ are independently hydrogen, halogen $C_{1-6}$ alkyl, or haloalkyl; $R_4$ is hydrogen; $C_{1-4}$ alkyl, alkenyl, alkoxy, haloalkyl; $C_{1-2}$ alkylamino, $C_{1-2}$ alkylthio, $C_{3-4}$ cycloalkyl, $C_{2-6}$ alkoxyalkyl, $C_{2-6}$ alkylthiomethyl, amino, phenoxy, phenamino, or furan and $R_5$ is hydrogen or $C_{1-4}$ alkyl.

Preferred species of the compounds of the present invention include: N-[[(chloroacetyl)(2-methyl-1-(1-methylethyl)-1-propenyl)amino]methyl]3-methoxypropanamide; N-[[(chloroacetyl)(2-methyl-1-(1-methylethyl)-1-propenyl)amino]methyl]-2-propenamide; and N-[[(chloroacetyl)(2-methyl-1-(1-methylethyl)-1-propenyl)amino]methyl]-cyclopropane-carboxamide.

The term "alkyl" refers to both straight chain and branched chain alkyl radicals.

The term "alkenyl" refers to both straight chain and branched chain alkenyl groups of the type $-C_nH_{2n-1}$.

The term "alkoxy" refers to both straight chain and branched chain alkoxy radicals containing alkyl or alkenyl groups as defined above.

The term "alkylthiomethyl" refers to a methyl group substituted by an alkylthio group.

The term "haloalkyl" refers to an alkyl group substituted by one or more halogen atoms, e.g., chloromethyl, bromomethyl, dichloroethyl, trifluoromethyl and the like. Preferably, trichloromethyl is avoided.

The term "phenamino" refers to both substituted and unsubstituted radicals of the formula phenyl $-NR_c$ where $R_c$ is hydrogen or alkyl.

In general, the selection of other types of substituents for $R_1$–$R_4$ is not critical to the method of the present invention and it is contemplated that other substituents such as aryl, carboxy, carboalkoxy, heteroaryl and the like would be equivalent to the compounds used in the method of the present invention.

The method of the present invention involves application of an effective plant-regulating, non-lethal amount of the compounds of the present invention to the plant locus of the turf grass. Regulating the growth of turf grass involves altering the natural growth of the turf grass to enhance various horticultural features of the grass. As employed herein, the term "natural growth" designated the normal life cycle of the grass in accordance with its genetics and environment in the absence of artificial, external influences. Regulation of the growth of turf grass can include retarding the amount of natural vegetative growth of the grass and/or retarding or reducing the natural formation of seedheads in turf grass. The regulation of natural growth of turf grass does not include killing or herbicidal action. By application to the "plant locus" is meant application to the plant's growing medium, such as the soil, as well as to the plant parts, such as roots, stems, and leaves. Preferably, the compounds are applied to establish turf grass. Application of the compounds to emerging seedlings may result in injury.

It is believed that the compounds of the present invention are absorbed into the plant through the roots. Therefore, it is desirable after application of the compounds of the present invention to the turf to water the turf to thereby wash the compounds into the soil. Watering of the turf is conveniently done within a short period of time after applying the compounds, e.g., within from about 3 hours to about 48 hours. A sufficient amount of water should be utilized to transport the compounds to the root zone. Depending upon the type and composition of the soil, conveniently about ¼ inch to about 1 inch of water is utilized.

In selecting an appropriate regulating amount of the compound of the present invention, it will be recognized that the effective regulating amount will vary with the plant species being treated, its stage of development, the specific compound being utilized, and the type of regulating effect being sought. The degree of regulating effect will vary with each species depending upon the absorption, translocation, and biological activity of the compound towards the species. An effective regulating amount will normally vary from about 0.1 to about 10 lbs. per acre. Conveniently a rate of from about 0.5 to about 5 lbs. per acre will be utilized. However, those skilled in the art will be able to determine an effective regulating amount of the compound for each species of turf grass and each specified compound.

In order to maximize the amount of regulation of the growth of turf grass, it is advantageous to apply the compounds of the present invention to the turf grass during the period beginning with green-up and prior to initiation of seedheads. "Green-up" is the transition of turf grass from dormancy (winter phase) to the active growth phase. "Initiation of seedheads" in the turf grass is defined as the physical appearance of seedheads at the base of the turf grass stem. Generally, it is preferred to apply the compounds of the present invention to the turf grass at about 75% to 100% green-up. Application of the compounds to the turf grass prior to initiation of green-up may result in retarding the green-up of the grass. Application of the compounds after initiation of seedheads will render them substantially ineffective in retarding the growth of seedheads. However, the compounds will still retard the vegetative growth of the turf grass. Those skilled in the art will be able to apply the compounds of the present invention to the turf grass at the appropriate time. For the homeowner, the application of the compound to the turf grass may be conveniently made after the first mowing of the grass.

The compounds of the present invention appear to regulate the growth of turf grass by inhibiting new tiller elongation growth for a limited period of time and also inhibit further growth of established tillers for a limited period of time. However, it is to be understood that each compound may not produce identical regulatory effects on each species or at every rate of application. Further, the visible morphological changes observed may result from a variety of physiological alterations by use of each of the compounds of the present invention.

One process for preparing the compounds of the present invention comprises reacting the corresponding 2-chloro-N-(alkoxymethyl)-N-alken-1-yl-acetamide with the desired nitrile generally in accordance with the procedure of the well-known Ritter reaction. Conveniently, the acetamide is mixed with a molar excess of the nitrile, e.g., 1.5 to 3 molar equivalents of nitrile per molar equivalent of acetamide, and this mixture is added slowly to cooled concentrated sulfuric acid, e.g., at a temperature of about 0° C. Alternatively, the nitrile and the acetamide can be added sequentially to the cooled sulfuric acid. After the addition the reaction mixture is stirred and allowed to warm to room temperature over a period of time, e.g., 2 hours. The product may be separated from the reaction mixture by standard laboratory procedures. Conveniently, the product can be separated by extraction with a suitable organic solvent, such as methylene chloride or ethyl acetate. The organic layer can be washed with water or salt water and dried over a suitable dry agent, such as magnesium, sulfate, or potassium carbonate. The crude product can then be purified by recrystallization, chromatography, distillation or the like.

An alternative process for making compounds of the present invention comprises reacting the corresponding 2-chloro-N-chloromethyl-N-alken-1-yl-acetamide with the desired nitrile generally in accordance with the procedure of the Ritter reaction.

An improved process for making the formamidomethyl acetamides of the present invention is disclosed and claimed in a copending, commonly assigned application entitled A Process For Preparation of N-(formamidomethyl)acetanilides, Ser. No. 701,273, filed concurrently herewith. The process generally involves reacting the corresponding N-(halomethyl)acetamide with an excess of formamide at an elevated temperature up to about 100° C. for a short period of time, eg. two hours. The product can be separated and purified as noted above.

The N-(N-alkyl amidomethyl)acetamide can be made by reacting the corresponding unsubstituted N-(amidomethyl)acetamide with a suitable alkylating agent in the presence of a base and a phase transfer catalyst. Suitable alkylating agents are alkyl sulfates, e.g., dimethylsulfate, haloalkyl alkyl ethers, halides of aliphatic and arylalkyl aromatic compounds, e.g., methyl iodide and benzyl bromide. Suitable bases are alkali metal hydroxides, e.g., sodium hydroxide and alkaline earth hydroxides. Suitable phase transfer catalysts are those that will form an ion pair with the cation of the phase transfer catalyst. Therefore, useful catalysts are those containing organic-soluble cations such as those enumerated in U.S. Pat. No. 3,992,432, including ammonium, phosphonium and sulfonium slats. Exemplary phase transfer catalysts include quaternary ammonium salts, e.g., aryl or aralkyl trialkyl ammonium halide salts such as benzyl triethyl ammonium bromide or chloride.

The reaction is conveniently run in an inert solvent. Suitable inert solvents include dichloromethane, benzene, chlorobenzene, tetrahydrofuran, dimethyl sulfoxide, dimethylformamide, toluene or diethyl ether.

The unsubstituted acetamide is conveniently mixed with a molar excess of the alkylating agent, e.g., 1.1 to 1.5 molar equivalent excess in a substantial molar excess of base, e.g., 5 to 10 molar equivalent excess. Conveniently, the base is added with stirring to a cooled mixture of the acetamide, alkylating agent, catalyst and inert solvent. After the addition, the mixture is mixed for a period of time, e.g., 1 hour, conveniently at room temperature. The product can be separated from the reaction mixture using standard laboratory procedures.

An alternative method for making the N-alkyl-N-(amidomethyl)acetamide compounds is disclosed in U.S. Pat. No. 3,769,301 which is incorporated herin by reference.

The starting acetamides can be prepared in accordance with known procedures. The starting nitriles are either commercially available or may be prepared according to the procedures set forth in the chemical literature.

The following examples are presented to illustrate the present invention as well as some of the various embodiments of the invention. These examples are presented as being illustrative of the invention and are not intended to be a limitation as to the scope thereof.

EXAMPLE 1

Preparation of N-[(Acetylamino)Methyl]-2-Chloro-N-[2-Methyl-1-(1-Methyl-Ethyl)-1-Propenyl]Acetamide To a stirred solution of 36 gm of concentrated $H_2SO_4$ at 5° C. was added 8.7 ml of acetic anhydride, and the mixture was stirred in the cold for about 0.5 hours. Acetonitrile (5.35 gm) was added, the solution was stirred for 5 minutes, and then 6.81 gm of N-methoxymethyl-2-chloro-N-[2-methyl-1-(1-methyl-ethyl)-1-propenyl]-acetamide was added. The reaction mixture was allowed to warm to room temperature over 4 hours and then partitioned between 100 ml of methylene chloride and 100 ml of $H_2O$. The organic layer was washed with 75 ml of $H_2O$, then 75 ml of saturated NaCl, and dried over $MgSO_4$. Filtration and concentration gave an off-white solid which was washed through a 5 cm plug of silicagel with 50% ethyl acetate in hexane to afford 3.6 gm of product as a white solid (m.p. 113°–114° C.). (48% yield) Analysis for $C_{12}H_{21}ClN_2O_2$:

|  | C | H | N |
|---|---|---|---|
| Calculated | 55.27 | 8.12 | 10.74 |
| Found | 55.19 | 8.15 | 10.70 |

EXAMPLES 2–5

Following substantially the same procedures described in Example 1 but substituting the appropriate starting materials and reaction conditions, other compounds according to the generic formula are prepared. The same or equivalent solvents, catalysts, etc., together with appropriate reaction times and temperatures, are readily used in preparing these compounds. Typical other compounds prepared in accordance with the above procedures are shown in Table I together with certain physical properties.

TABLE I

| Example No. | Compound | Emperical Formula | B.P. °C. (mm Hg) | Element | Analysis Calculated | Found |
|---|---|---|---|---|---|---|
| 2 | N—[[(chloroacetyl)(2-methyl-1-(1-methylethyl)-1-propenyl)amino]methyl]3-methoxy-propanamide | $C_{14}H_{25}Cl_1N_2O_3$ | 66–68° C. (M.P.) | C<br>H<br>N | 55.16<br>8.26<br>9.19 | 55.14<br>8.25<br>9.05 |
| 3 | N—[[(chloroacetyl)(2-methyl-1-(1-methylethyl)-1-propenyl)amino]methyl]-2-propenamide | $C_{13}H_{21}Cl_1N_2O_2$ | 79–80° C. (M.P.) | C<br>H<br>N | 57.20<br>7.76<br>10.27 | 57.40<br>7.76<br>10.26 |
| 4 | N—[[(chloroacetyl)(2-methyl-1-(1-methylethyl)-1-propenyl)amino]methyl]-cyclopropane-carboxamide | $C_{14}H_{23}Cl_1N_2O_2$ | 114–115° C. (M.P.) | C<br>H<br>N | 57.60<br>8.10<br>9.76 | 57.33<br>7.77<br>10.06 |
| 5 | N—[(acetylamino)methyl]-2-chloro-N—(1,2-dimethyl-1-propenyl)-acetamide (CP 107727) | $C_{10}H_{17}Cl_1N_2O_2$ | 126–127° C. (M.P.) | C<br>H<br>N | 50.61<br>7.36<br>12.04 | 50.99<br>7.16<br>11.91 |

EXAMPLE 6

In this test a number of pots were planted in the greenhouse with Kentucky-31 Fescue and were grown for about 8 weeks. During this period the pots were fertilized and water and treated for disease on a regular basis. After about 3 weeks the turf grass was cut to a uniform height of about 6 cm and maintained at this height. The compounds to be applied were formulated in water and a suitable organic solvent, such as acetone or alcohol, and about 0.25% of a surface-active agent was added. After application of the compound, the pots were returned to the greenhouse and watered as before. The heights of the plants in the control and test pots were measured and recorded after about 2 weeks.

In the following tables, the reduction or retardation in the rate of turf grass growth induced by the compounds of the present invention is expressed in terms of the growth of the treated turf grass during the test period relative to the growth of untreated turf grass during the test period. The percent of controls growth (PCG) is determined in accordance with the general equation:

$$PCG = \frac{\text{Growth of Treated Turf}}{\text{Growth of Untreated Turf}} \times 100$$

The growth of the treated and untreated turf grass as used in the above equation is the difference in the height of the turf grass before the test and the height of the treated or untreated turf grass at the end of the test period. Tables II and III summarize the results of the tests conducted in accordance with this procedure.

TABLE II

| Compound of Example No. | Rate (kg/ha) | PCG |
|---|---|---|
| 1 | 5.6 | 62 |
| 2 | 5.6 | 29 |
| 3 | 5.6 | 40 |
| 4 | 5.6 | 41 |
| 5 | 5.6 | *58 |

*Average of two tests

TABLE III

| Compound of Example No. | Rate (kg/ha) | PCG |
| --- | --- | --- |
| 2 | 5.6 | 53 |
|   | 2.24 | 56 |
|   | 0.56 | 91 |
| 3 | 5.6 | 44 |
|   | 2.24 | 44 |
|   | 0.56 | 79 |
| 4 | 5.6 | 46 |
|   | 2.24 | 57 |
|   | 0.56 | 63 |

As illustrated by the above example, one result of applying the compounds of the present invention to turf grass is reduced height of the turf grass relative to the height of the untreated turf grass. Other desirable results include increased density of the turf grass and darkening of the color of systems of the turf grass.

The compounds of the present invention can be used with adjuvants in liquid or solid form. The compositions are prepared by admixing the compounds with an adjuvant including diluents, extenders, carriers, and conditioning agents to provide compositions in the form of finely-divided particulate solids, granules, pellets, solutions, dispersions, or emulsions. Thus, they can be used with an adjuvant, such as a finely-divided solid, a liquid of organic origin, water, a wetting agent, a dispersing agent, an emulsifying agent, binder, carrier or any suitable combination of these.

The compounds of this invention can also be in the form of liquids and wettable powders. These preferably contain as a conditioning agent one or more surface-active agents in amounts sufficient to render a given compound readily dispersible in water or in oil. The incorporation of a surface-active agent into the compound can enhance its efficacy. By the term "surface-active agent" it is understood that wetting agents, dispersing agents, suspending agents, and emulsifying agents are included therein. Anionic, cationic, and nonionic agents can be used.

Preferred wetting agents are alkyl benzene and alkyl naphthalene sulfonates, sulfonated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium salts of lignin sulfonates, polymeric alkyl, naphthalene sulfonates, sodium naphthalene sulfonate, and the polymethylene bisnaphthalene sulfonate.

Wettable powders or dispersable granules are water-dispersible compositions containing one or more active ingredients, an inert solid extender, and one or more wetting and dispersing agents. The inert solid extenders are usually of mineral origin, such as the natural clays, diatomaceous earth, salts and synthetic minerals, derived from silica and the like. Examples of such extenders include kaolinites, attapulgite clay, salts and synthetic magnesium silicate. The wettable powder compositions of this invention usually contain from about 0.5 to 90 parts (preferably from 5 to 50 parts) of active ingredient, from about 0.25 to 25 parts (preferably 1 to 15 parts) of wetting agent, from about 0.25 to 25 parts (preferably 1.0 to 15 parts) of dispersant, and from 5 to about 95 parts (preferably 5 to 50 parts) of inert solid extender, all parts being by weight of the total composition. When required, from about 0.2 to 2.00 parts of the solid inert extender can be replaced by a corrosion inhibitor or antifoaming agent or both.

Aqueous suspensions or emulsions may be prepared by stirring an aqueous mixture of a water-insoluble active ingredient and an emulsification agent until uniform and then homogenized or milled to give stable emulsion or suspension of very finely-divided particles. The resulting concentrated aqueous suspension is characterized by its extremely small particle size, so that when diluted and sprayed, coverage is very uniform. Suitable concentrations of these formulations contain from about 25% to 60%, preferably 35% to 50% by weight, of active ingredient, the upper limit being determined by the properties of the active ingredient.

In another form of aqueous suspensions, a water-immiscible component is encapsulated to form microencapsulated phase dispersed in an aqueous phase. In one embodiment, minute capsulates are formed by bringing together an aqueous phase containing a lignin sulfonate emulsifier and a water-immiscible chemical and polymethylene polyphenylisocyanate, dispersing the water-immiscible phase in the aqueous phase followed by addition of a polyfunctional amine. The isocyanate and amine compounds react to form a solid urea shell wall around particles of the water-immiscible chemical, thus forming microcapsules thereof. Generally, the concentration of the microencapsulated material will range from about 480 to 700 g/l of total composition, preferably 480 to 600 g/l. The microencapsulation process referred to here is described in more detail in U.S. Pat. No. 4,280,833.

Concentrates are usually solutions of the active ingredients in water-immiscible or partially water-immiscible solvents together with a surface active agent. Suitable solvents for the active ingredients of this invention include dimethylformamide, dimethylsulfoxide, N-methylpyrrolidone, hydrocarbons, and water-immiscible ethers, esters, ketones, or aromatics. However, other high strength liquid concentrates may be formulated by dissolving the active ingredient in a solvent then diluting, e.g., with kerosene, to spray concentration.

The concentration compositions herein generally contain from about 0.1 to 95 parts (preferably 35 to 60 parts) active ingredient, about 0.25 to 50 parts (preferably 1 to 25 parts) surface active agent, and where required, about 4 to 94 parts solvent, all parts being by weight based on the total weight of emulsifiable oil.

Granules are physically stable particulate compositions comprising the active ingredients adhering to or distributed through a basic matrix of an inert, particulate extender. In order to aid leaching of the active ingredient from the particulate, a surface active agent, such as those listed hereinbefore, can be present in the composition. Natural clays, pyrophyllites, illite, gypsum, and vermiculite are examples of operable classes of particulate mineral extenders. The preferred extenders are the porous, absorptive, preformed particles, such as preformed and screened particulate attapulgite or heat-expanded, particulate vermiculite, and the finely-divided clays, such as kaolin clays, hydrated attapulgite, or bentonitic clays. These extenders are sprayed or blended with the active ingredient to form the herbicidal granules.

Granular compositions useful in this invention may contain from about 0.1 to about 30 parts, preferably from about 0.5 to 10 parts by weight of active ingredient per 100 parts by weight of clay, and 0 to about 5 parts by weight of surface active agent per 100 parts by weight of particulate clay.

The compounds can also be added together with other additaments, for example, other growth regulators fertilizers, herbicides, pesticides, safeners and the like used as adjuvants or in combination with any of the above-described adjuvants. 35 to 60 parts) active ingredient, about 0.25 to 50 parts (preferably 1 to 25 parts) surface active agent, and where required, about 4 to 94 parts solvent, all parts being by weight based on the total weight of emulsifiable oil.

Granules are physically stable particulate compositions comprising the active ingredients adhering to or distributed through a basic matrix of an inert, particulate extender. In order to aid leaching of the active ingredient from the particulate, a surface active agent, such as those listed hereinbefore, can be present in the composition. Natural clays, pyrophyllites, illite, gypsum, and vermiculite are examples of operable classes of particulate mineral extenders. The preferred extenders are the porous, absorptive, preformed particles, such as preformed and screened particulate attapulgite or heat-expanded, particulate vermiculite, and the finely-divided clays, such as kaolin clays, hydrated attapulgite, or bentonitic clays. These extenders are sprayed or blended with the active ingredient to form the herbicidal granules.

Granular compositions useful in this invention may contain from about 0.1 to about 30 parts, preferably from about 0.5 to 10 parts by weight of active ingredient per 100 parts by weight of clay, and 0 to about 5 parts by weight of surface active agent per 100 parts by weight of particulate clay.

The compounds can also be added together with other additaments, for example, other growth regulators fertilizers, herbicides, pesticides, safeners and the like used as adjuvants or in combination with any of the above-described adjuvants.

Although this invention has been described with respect to specific embodiments, the details hereof are not to be construed as limitations, for it will be apparent that various equivalents, changes and modifications may be resorted to without departing from the spirit and scope thereof and it is understood that such equivalent embodiments are intended to be included within the scope of this invention.

We claim:

1. A method for retarding the growth of turf grass which comprises applying to said turf grass an effective growth retarding amount of a compound of the formula:

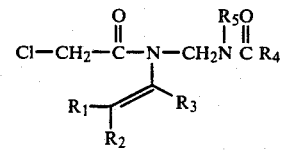

wherein $R_1$, $R_2$, and $R_3$ are independently hydrogen, halogen $C_{1-6}$ alkyl, or haloalkyl; $R_4$ is hydrogen; $C_{1-4}$ alkyl, alkenyl, $C_{3-4}$ cycloalkyl, or $C_{2-6}$ alkoxyalkyl, and $R_5$ is hydrogen or $C_{1-4}$ alkyl.

2. A method according to claim 1 wherein $R_4$ is $C_{1-4}$ alkenyl, $C_{3-4}$ cycloalkyl or $C_{2-6}$ alkoxyalkyl.

3. A method according to claim 3 wherein $R_4$ is $C_{2-6}$ alkoxyalkyl.

4. A method according to claim 1 wherein $R_5$ is hydrogen.

5. A method according to claim 1 wherein $R_5$ is hydrogen.

6. A method according to claim 1 wherein said compound is N-[[(chloroacetyl)(2-methyl-1-(1-methylethyl)-1-propenyl)amino]methyl]3-methoxy-propanamide.

7. A method according to claim 1 wherein said compound is N-[[(chloroacetyl)(2-methyl-1-(1-methylethyl)-1-propenyl)amino]methyl]-2-propenamide.

8. A method according to claim 1 wherein said compound is N-[[(chloroacetyl)(2-methyl-1-(1-methylethyl)-1-propenyl)amino]methyl]-cyclopropane-carboxamide.

* * * * *